(12) United States Patent
Huff et al.

(10) Patent No.: US 6,316,387 B1
(45) Date of Patent: Nov. 13, 2001

(54) SYNERGISTIC ACTIVE COMPOUND COMBINATIONS FOR CONTROLLING HARMFUL PLANTS IN CROPS OF USEFUL PLANTS

(75) Inventors: Hans Philipp Huff, Eppstein; Jean-Michel Wolff, Hofheim; Kurt Grüninger, Bad Wurzach; Hermann Bieringer, Eppstein, all of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 08/907,652

(22) Filed: Aug. 8, 1997

(30) Foreign Application Priority Data

Aug. 12, 1996 (DE) ............................................. 196 32 424

(51) Int. Cl.$^7$ ........................ A01N 43/707; A01N 43/40; A01N 43/76; A01N 39/02
(52) U.S. Cl. ........................ 504/134; 504/130; 504/133; 504/135; 504/136; 504/138; 504/145; 504/146
(58) Field of Search .................................. 504/133, 134, 504/138, 135, 130, 136, 145, 146

(56) References Cited

U.S. PATENT DOCUMENTS

| | | | |
|---|---|---|---|
| 4,047,929 | 9/1977 | Schmidt et al. | 504/135 |
| 4,130,413 | * 12/1978 | Handte et al. | 548/329 |
| 4,336,057 | 6/1982 | Bieringer et al. | 504/132 |

FOREIGN PATENT DOCUMENTS

| | | |
|---|---|---|
| 18148/83 | 8/1983 | (AU) . |
| 79843/87 | 3/1990 | (AU) . |
| 1170854 | 7/1984 | (CA) . |
| 1199194 | 1/1986 | (CA) . |
| 2055866 | 5/1992 | (CA) . |
| 2537290 | 3/1977 | (DE) . |
| 2815287 | 10/1979 | (DE) . |
| 0302983 | 2/1989 | (DE) . |
| 0043800 | 1/1982 | (EP) . |
| 0086392 | 8/1983 | (EP) . |
| 0103732 | 3/1984 | (EP) . |
| 3444860 | 6/1986 | (EP) . |
| 0487454 | 5/1992 | (EP) . |
| 0614608 | 9/1994 | (EP) . |
| 2167959 | 6/1986 | (GB) . |

OTHER PUBLICATIONS

Chemical Abstract No. 94:97882r(1981).
Chemical Abstract No. 115:177353m(1991).
Chemical Abstract No. 116:2237v(1992).
Chemical Abstract No. 107:72722n(1987).
Chemical Abstract No. 91: 135430q(1979).
Database Cropu STN–International, E.C. Hughes et al. entitled "Postemergence Herbicide Trails on Potatoes Variety Red Lapsoda", No. XP002048061, 1997.
J.D.A. Wevers, Bd. 56, No. 3a, 1991, pp. 611–615 entitled "Low Dosage Systems for Controlling Broadleaf and Annual Weeds in Sugarbeet", No. XP002048310.
David L. Jordan, Bd. 9, No. 4, 1995, pp. 741–747, entitled "Influence of Adjuvants 1,2 on the Antagonism of Graminicides by Broadleaf Herbicides", No. XP002048311.
Chemical Abstracts, vol. 111, No. 5, Jul. 31, 1989, by Stanger et al., entitled "Italian Ryegrass (Lolium Multiflorum) Accessions Tolerant to Diclofop", No. XP002048060.
Holt, Neal W. et al., "Annual Canarygrass (Phalaris Canariensis) Tolerance and Weed Control Following Herbicide Application," Weed Science, vol. 35, No. 5, pp. 673–677, 1987.*
Farmchemicals Handbook '95, Meister Publishing Co., Ohio, vol. 81, pp. C163, C164, C249, 1995.*
Chemical Abstracts 104: 837156, 1986.*
Chemical Abstracts 112: 173984, 1990.*

* cited by examiner

Primary Examiner—John Pak
(74) Attorney, Agent, or Firm—Frommer Lawrence & Haug LLP

(57) ABSTRACT

The present invention relates to the use of a herbicidal combination for the selective control of harmful grasses from the group consisting of Phalaris supp. and Lolium supp. in crops of useful plants, each combination comprising:

A) one or more compounds from the group of the 1,2,4-triaznones; and

B) one or more compounds from the group consisting of (het)aryloxyphenoxy-propionic acid derivatives and cyclohexanedione oximes, and to the novel herbicidal compositions defined in the description suitable for the use according to the invention.

The compositions are also suitable for reducing the application rate and the phytotoxicity of the individual herbicides in the crops.

7 Claims, No Drawings

SYNERGISTIC ACTIVE COMPOUND COMBINATIONS FOR CONTROLLING HARMFUL PLANTS IN CROPS OF USEFUL PLANTS

Synergistic active compound combinations for controlling harmful plants in crops of useful plants.

The invention relates to the field of crop protection agents, and in particular to combinations of groups of active compounds having different modes of action and types of activity, which are outstandingly suitable for use against harmful plants in crops of useful plants.

In many crops of useful plants, grasses are undesirable competitors which can be controlled only with considerable difficulty and at high costs. They germinate and grow in the soil over prolonged periods of time and can therefore only be effectively controlled with herbicides having foliar and soil action.

Examples of important weed grasses which occur in crops of useful plants all over the world and which are of high economic importance are:

Alopecurus myosuroides, Avena fatua and other forms of wild oats, Lolium spp., Phalaris spp., Setaria spp., Echinochloa spp., Poa spp., Bromus spp., Elymus repens, Sorghum spp. and others such as, for example, Agrostis, Panicum, etc.

It has been known for long that compounds from the group of the 1,2,4-triazinones, the (het)aryloxyphenoxypropionates and the cyclohexanedione oximes have excellent herbicidal activity, even if their preferred application in different crops takes place at in some cases considerably different application rates.

EP-A-0 614 608 describes synergistic herbicidal compositions for controlling slender foxtail which comprise certain combinations of (het)aryloxyphenoxypropionates and herbicides of other types of action. These described compositions are generally well suited for controlling grasses such as wild oats (Avena fatua) or slender foxtail (Alopecurus myosuroides) or weeds such as common chickweed (Stellaria media) in crops of cereals.

The compounds of the group of the 1,2,4-triazinones are known as selective systemic herbicides which act as inhibitors of photosynthesis and which are taken up predominantly via the roots, but also via the leaves. Hitherto, the herbicide metribuzin could be used in cereals and maize only at limited application rates; higher dosages, in particular on light soils and at high levels of precipitation, are not fully tolerated. On the other hand, metribuzin is an agent which is widely used in many countries in crops such as soybeans and potatoes. Higher dosages, as they are generally needed in cereals and maize for controlling grasses, are often not acceptable since they are not fully selective. Generally, the activity against many grasses is not satisfactory, so that in practice mixtures with other soil herbicides such as, for example, alachlor, metolachlor or dimethenamide are used to control the grasses with better effectiveness.

Herbicides from the group of the(het)aryloxyphenoxypropionic acids and also of the cyclohexanedione oximes are in each case acetyl-CoA-carboxylase inhibitors and are particularly easily taken up via the leaves. They are used by the post-emergence method for controlling grasses in all important crops. Some of the important ones, such as diclofop, fenoxaprop, clodinafop and tralkoxydim, can also be used for controlling grasses in cereals, compositions based on fenoxaprop and clodinafop generally being used in combination with safeners, i.e. herbicidal antidotes.

Recently, some of these grasses have become difficult to control since, owing to the repeated application of herbicidally active compounds, resistant forms, or forms which have a significantly reduced susceptibility towards these groups of active compounds, have emerged. In this case, it is no longer possible to use the corresponding herbicides at application rates which ensure the desired herbicidal effect without causing considerable damage to the crops. Depending on the type of grass and herbicide, the resistance increase can vary considerably and can be so high that even amounts of 2 to 10 times the normal application rate are no longer sufficiently effective.

In biological greenhouse trials and free-range trials, it has now been found that certain, partly novel, herbicidally active compound combinations exhibit surprisingly high synergistic activities which far exceed expectations, and that they are at the same time very well tolerated by the crops. Additionally, it is possible to selectively control harmful grasses of economic importance which could hitherto not be controlled by any of the individual active compounds by employing the present herbicidal combinations. This also applies to grasses which have become resistant against one of the active compounds in question and which have therefore caused new problems in agricultural practice. Using the combinations according to the invention, it is once again possible to control even those species efficiently. Owing to their properties with respect to their spectrum of activity and their effectiveness, which are highly superior to the known herbicidal compositions, it is possible to employ the novel synergistic active compound combinations at considerably reduced application rates, so that, in addition to the advantage of improved cultivation of the useful plants, further economic and ecologic advantages can be obtained.

The present invention, accordingly, provides for the use of a herbicidal combination for the selective control of harmful grasses from the group consisting of Phalaris spp. and Lolium spp. in crops of useful plants, the combination comprising A) one or more compounds from the group of the 1,2,4-triazinones and B) one or more compounds from the group consisting of (het)aryloxyphenoxypropionic acid derivatives and cyclohexanedione oximes.

Examples of suitable compounds are listed below (cf. The Pesticide Manual, 10th. Edition, British Crop Protection Council, 1994):

compounds of type A: metribuzin and metamitron;

compounds of type B (acetyl-CoA-carboxylase inhibitors): (het)aryloxyphenoxypropionates, for example fenoxaprop, fenoxaprop-P, clodinafop, haloxyfop, quizalofop, quizalofop-P, diclofop, fluazifop, fluazifop-P, propaquizafop, isoxapyrifop and the ($C_1$–$C_4$)-alkyl esters, ($C_2$–$C_4$)-alkenyl esters or ($C_2$–$C_4$)-alkinyl esters of the abovementioned herbicides, and cyclohexanedione oximes, for example alloxydim, sethoxydim, cloproxydim, cycloxydim, clethodim and tralkoxydim.

Preference is given to the use of those herbicidal combinations according to the invention which comprise as compound A) metribuzin and B) one or more compounds of the group consisting of fenoxaprop, fenoxaprop-P, clodinafop, haloxyfop, quizalofop, quizalofop-P, diclofop, fluazifop-P, propaquizafop, isoxapyrifop and esters thereof and tralkoxydim; very particular preference is given to the use of the abovementioned compositions in crops of cereals.

Some of the herbicide combinations which can be used according to the invention are already known; their suitability for use against the abovementioned grasses which have developed resistance against some of the herbicides has not been known.

Known combinations of herbicides are:

a) metribuzin in combination with fenoxaprop-(P) ester [see the abovementioned EP-A-614608]

b) metribuzin in combination with the cyclohexanedione herbicide 5-(1-methylthiocyclopropan-1-yl)-2-[1-(trans-3-chloroallyloximino)-propionyl]cyclohexane-1,3-dione [cf. EP-A-487454]; the combination is recommended for controlling Digitaria sanguinalis, Sorghum halepense, Alopecurus myosuroides, Setaria faberi and Echinochloa crusgalli in dicotyledonous cultures such as soybean, sugar beet, rapeseed, cotton and vegetables.

c) metribuzin in combination with diclofop-methyl; the action on Avena fatua [Chem. Abstracts 94:97882r] and the selective action on Eleusine indica in Cynodon spp. (Bermudagrass) [Chem, Abstracts 115:177353m] is described.

d) metribuzin in combination with sethoxydim or fluazifop-P-butyl [Chem. Abstracts 116:2237v]; the action on Amaranthus retroflexus, Eleusine indica and Digitaria sanguinalis is described.

e) metribuzin in combination with fluazifop-P-butyl, haloxyfop-methyl, quizalofop-ethyl or sethoxydim [Chem. Abstracts 110:187715s]; the action on Avena fatua, Hordeum vulgare and Sinapis arvensis is described.

f) metribuzin in combination with haloxyfop and use thereof for controlling harmful plants in okra crops [Chem. Abstracts 107:72722n].

g) metamitron in combination with diclofop-methyl and their increased phytotoxic action in sugar beet crops [Chem. Abstracts 91:135430q].

The invention also provides novel herbicidal compositions suitable for the use according to the invention, which comprise an effective amount of a combination of A) one or more compounds from the group of the 1,2,4-triazinones and B) one or more compounds from the group consisting of (het)aryloxyphenoxypropionic acid derivatives and cyclohexanedione oximes, except for compositions which comprise as combination of herbicidally active compounds A) metribuzin in combination with B) a herbicide from the group consisting of fenoxaprop, fenoxaprop-P or alkyl esters thereof, diclofop-methyl, fluazifop-P-butyl, haloxyfop-methyl, quizalofop-ethyl, sethoxydim and 5-(1-methylthiocyclopropan-1-yl)-2-[1-(trans-3-chloroallyloximino)propionyl]cyclohexane-1,3-dione, or A) metamitron in combination with B) diclofop-methyl.

Preference is given to those novel herbicidal compositions which comprise the abovementioned herbicides, except for compositions which comprise as combination of herbicidally active compounds A) metribuzin in combination with a herbicide from the group consisting of B) fenoxaprop, fenoxaprop-P or alkyl esters thereof, diclofop-methyl, fluazifop-butyl, fluazifop-P-butyl, haloxyfop-methyl, quizalofop-ethyl, quizalofop-P-ethyl, clodinafop-propargyl, sethoxydim and 5-(1-methylthiocyclopropan-1-yl)-2-[1-(trans-3-chloroallyloximino)propionyl]cyclohexane-1,3-dione, or A) metamitron in combination with B) diclofop-methyl.

Particular preference is given to those of the abovementioned herbicidal compositions according to the invention which comprise as compound of type A) metribuzin and as compound of type B) fenoxaprop, fenoxaprop-P, clodinafop, haloxyfop, quizalofop, quizalofop-P, diclofop, fluazifop-P, propaquizafop, isoxapyrifop, esters of the abovementioned herbicides or tralkoxydim or more than one of the abovementioned herbicides of type B).

The present invention also provides a method for controlling harmful plants from the group consisting of Phalaris spp. and Lolium spp. in crops of useful plants, which comprises applying the components of the abovementioned herbicidal composition together, or separately at different times, to the plants, their seeds and/or the area under cultivation, in particular in crops of cereals.

The invention also provides a method for protecting crops of useful plants against the phytotoxic action of at least one herbicide from the group of the 1,2,4-triazinones, (het) aryloxyphenoxypropionic acid derivatives and/or cyclohexanedione oximes, which comprises applying the herbicide to the crops, their seeds and/or the area under cultivation in the form of a composition according to the invention, in particular in crops of cereals.

Finally, the invention provides the use of the herbicidal combinations defined by the compositions according to the invention for reducing the phytotoxicity in crops of useful plants which occurs when the components included in said herbicidal combinations are applied individually, in particular in crops of cereals.

The herbicidally active compounds which exist as enantiomers, for example those of the group of the (het) aryloxyphenoxypropionates, can be present in the form of their racemic mixtures and as their biologically active isomers. They can be employed either as free acids, salts thereof or, preferably, as esters.

The abovementioned compounds are known from the literature, for example The Pesticide Manual, 10th Edition, British Crop Protection Council, 1994.

The active compound combinations according to the invention have a very good action against economically important harmful grasses. In this context, a surprisingly low application rate of the herbicide A is sufficient to obtain, together with the herbicide B, very good effectiveness against grasses. This action of the combinations is synergistic and exceeds the expected additive effect by far. This activity increase allows a considerable reduction of the application rates of the individual active compounds. Such properties offer the user considerable advantages in the practice of controlling weeds. The user can control the harmful plants more cheaply, more rapidly, with less effort and more permanently and thus obtain higher yields from the crops.

In addition, very good control results are also obtained with grasses which have become partially resistant, i.e. unsusceptible to herbicides of type B applied on their own. The individual partners in the combination have no comparable good effect. The use of the present combinations therefore opens up fundamentally new, improved possibilities to control grasses which up to now could only be controlled with unsatisfactory results, or resistant grasses, very effectively.

The main areas of application for the use of the combinations are especially crops of cereals, but also broad-leaved crops such as soybeans, cotton, and likewise maize, rice and numerous other crops.

Even though the compositions according to the invention have an excellent herbicidal activity against harmful plants, crops are damaged only insignificantly, if at all. For these reasons, the compositions are particularly suitable for use in wheat for the selective control of undesirable vegetation, preferably Phalaris spp. and Lolium spp. vegetation.

If the active compound combinations are applied postemergence to the green parts of the plants, growth stops a very short time after the treatment. The weed plants remain at the growth stage of the point of time of application, or they die more or less quickly after a certain time, so that in this manner competition by the weeds, which is harmful to the crop plants, is eliminated at a very early point and in a sustained manner by the use of the novel compositions according to the invention.

The herbicidally active compounds of the combinations can be applied jointly (as a finished formulation or by the tank mix method), or they can be applied successively in a short interval of a few hours or days in any sequence desired.

The weight ratio of the herbicidally active compounds of the combinations can vary within wide limits and is preferably in the range from 50:1 to 1:50.

The mixing ratios of the different components can vary within wide limits. They depend in particular on the mixing partner employed, on the nature of the crops to be treated, on the development stage of the harmful grasses and on the climatic conditions. In each case, the optimum amounts of herbicide depend in particular on the active compound of type B used, and they can be determined by simple preliminary trials.

For economical reasons, the joint application is preferred, but a separate application can also be efficient and advantageous. Owing to the interaction of two different mechanisms of action and different ways of absorption, it may even be possible to achieve a better effectiveness by separate applications.

The compounds of type A or type B or their combinations can be formulated in various ways, depending on the prevailing biological and/or chemical-physical parameters. The active compound combinations according to the invention can be present either as mix formulations of the two components which are then diluted with water in a customary manner or applied as granules, or they are present as tank mixes which are prepared by joint dilution with water of the separately formulated components.

The compounds (combinations) can be formulated in various ways, depending on the prevailing biological and/or chemico-physical parameters. The following possibilities are suitable formulations: wettable powders (WP), emulsifiable concentrates (EC), aqueous solutions (SL), emulsions (EW), such as oil-in-water and water-in-oil emulsions, sprayable solutions or emulsions, oil- or water-based dispersions, suspoemulsions, dusts (DP), seed-dressing products, and in particular granules for broadcasting and soil application, water-dispersible granules (WG), ULV formulations, microcapsules and waxes.

These individual types of formulation are known in principle and are described, for example, in: Winnacker-K üchler, "Chemische Technologie" [Chemical Technology], Volume 7, C. Hauser Verlag Munich, 4th Ed. 1986; van Valkenburg, Pesticide Formulations, Marcel Dekker, N.Y., 2nd Edition 1972–73; K. Martens, Spray Drying Handbook, 3rd Edition, G. Goodwin Ltd. London.

The formulation auxiliaries required, such as inert materials, surfactants, solvents and other additives are also known and are described, for example, in: Watkins, Handbook of Insecticide Dust Diluents and Carriers, 2nd Edition, Darland Books, Caldwell N.J.; H.v. Olphen, Introduction to Clay Colloid Chemistry, 2nd Edition, J. Wiley & Sons, N.Y., Marsden, Solvents Guide; 2nd Edition, Interscience, N.Y. 1950; McCutcheon's, Detergents and Emulsifiers Annual, MC Publ. Corp., Ridgewood N.J.; Sisley and Wood, Encyclopedia of Surface Active Agents, Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-K üchler, "Chemische Technologie" [Chemical Technology], Volume 7, C. Hauser Verlag Munich, 4th Ed. 1986.

Based on these formulations, it is also possible to prepare combinations with other pesticidally active compounds, such as other herbicides, fungicides or insecticides, and fertilizers and/or growth regulators, for example in the form of a ready mix or a tank mix.

Wettable powders are preparations which are uniformly dispersible in water and which, besides the active compound, also comprise wetting agents, for example polyoxethylated alkylphenols, polyoxethylated fatty alcohols or fatty amines, alkanesulfonates, alkylbenzenesulfonates, and dispersants, for example sodium lignosulfonate, sodium 2,2'-dinaphthyl-methane-6,6'-disulfonate, sodium dibutylnaphthalenesulfonate or else sodium oleoylmethyltaurinate, in addition to a diluent or inert substance.

Emulsifiable concentrates are prepared, for example, by dissolving the active compound in an organic solvent, for example butanol, cyclohexanone, dimethylformamide, xylene, or else higher-boiling aromatics or hydrocarbons with the addition of one or more emulsifiers. Examples of emulsifiers which can be used are: calcium salts of alkyllaurylsulfonic acids such as calcium dodecylbenzenesulfonate, or nonionic emulsifiers such as fatty acid polyglycol esters, alkyllauryl polyglycol ethers, fatty alcohol polyglycol ethers, propylene oxide/ethylene oxide condensates, alkyl polyethers, sorbitan fatty acid esters, polyoxyethylene sorbitan fatty acid esters, or polyoxyethylene sorbitan esters.

Dusts are obtained by grinding the active compound with finely divided solid substances, for example talc, natural clays such as kaolin, bentonite and pyrophyllite, or diatomaceous earth.

Granules can be prepared either by spraying the active compound onto adsorptive granulated inert material or by applying active compound concentrates to the surface of carriers such as sand, kaolinites or of granulated inert material by means of binders, for example polyvinyl alcohol, sodium polyacrylate or else mineral oils. Suitable active compounds can also be granulated in the manner which is conventional for the production of fertilizer granules, if desired as a mixture with fertilizers.

Generally, the agrochemical preparations comprise 0.1 to 99 percent by weight, in particular 2 to 95% by weight, of active compounds A and/or B. The concentrations of active compounds A and B may vary in the formulations.

The active compound concentration in wettable powders is, for example, approximately 10 to 95% by weight, the remainder to 100% by weight being composed of customary formulation components. In the case of emulsifiable concentrates, the active compound concentration may amount to approximately 1 to 85% by weight, preferably 5 to 80% by weight. Formulations in the form of dusts comprise approximately 1 to 25% by weight, in most cases 5 to 20% by weight of active compound, and sprayable solutions comprise approximately 0.2 to 25% by weight, preferably 2 to 20% by weight of active compound. The active compound content of granules, for example waterdispersible granules, depends partly on whether the active compound is in liquid or solid form and on which granulation auxiliaries and fillers are being used. The active compound content generally amounts to between 5 and 90% by weight in the case of the water-dispersible granules, and to between 1 and 50%, preferably between 2 and 25%, in the case of granules for broadcasting.

In addition, the abovementioned formulations of active compounds comprise, if appropriate, adhesives, wetting agents, dispersants, emulsifiers, penetrants, solvents, fillers or carriers which are customary in each case.

For use, the formulations, which are in commercially available form, are, if appropriate, diluted in the customary manner, for example using water in the case of wettable powders, emulsifiable concentrates, dispersions and water-dispersible granules. Preparations in the form of dusts, granules for soil application or for broad casting and sprayable solutions are conventionally not diluted any further with other inert substances prior to use.

The required application rate of the mixtures varies depending on external factors such as temperature, humidity, the kind of the herbicide used, etc.

The examples below illustrate the invention, without imposing any limitations.

Biological Examples

Example 1
Free Range Trial, Control of Harmful Plants by the Post-Emergence Method In free-range trials, the combinations according to the invention were applied to 10 m² plots overgrown with grasses which are difficult to control, at the growth stage stated. 3 or 4 weeks later, the effectiveness of the herbicide treatments was scored visually in comparison with an untreated control, the assessment being carried out using a percent scale (0–100% efficacy).

TABLE 1

Control of Phalaris spp. (stage: begin of stocking)
Visual scoring 28 days after treatment.
Theoretical values calculated according to Colby in brackets.

| Herbicide | Dose [kg a.i./ha] | Visual scoring [%] |
|---|---|---|
| Fenoxaprop-P-ethyl | 0.090 | 73 |
| Metribuzin | 0.144 | 0 |
|  | 0.192 | 0 |
| Fenoxaprop-P-ethyl + | 0.090 + 0.048 | 85 (73) |
| Metribuzin | 0.090 + 0.096 | 91 (73) |
|  | 0.090 + 0.144 | 94 (73) |

TABLE 2

Control of Phalaris spp. of various degrees of resistance in *Triticum aestivum* (wheat), visual scoring 21 days after the treatment.
Theoretical values calculated according to Colby in brackets.

| Herbicide | Dose [kg a.i./ha] | A Visual scoring [%] Phalaris | wheat | B Visual scoring [%] Phalaris | wheat |
|---|---|---|---|---|---|
| Diclofop | 0.700 | 3 | 0 | 76 | 0 |
| Metribuzin | 0.048 | 15 | 4 | 28 | 0 |
|  | 0.144 | 53 | 5 | 31 | 0 |
| Diclofop + | 0.7 + 0.048 | 44 (18) | 4 | 99 (83) | 0 |
| Metribuzin | 0.7 + 0.096 | 81 (—) | 5 | 99 (—) | 0 |
|  | +0.144 | 88 (54) | 6 | — | — |

A: Application at the 2–4 leaf stage
B: Application at the 1–2 leaf stage

In all instances, a distinction was made in the combinations between the calculated degree of action and the degree of action found. The calculated expected theoretical degree of action of a combination can be approximately estimated using the Colby formula (S. R. Colby, Weeds 15 (1967), pages 20–22, "Calculations of synergistic and antagonistic responses of herbicide combinations."). For combinations of two compounds, this formula is:

$$E = X + Y - \frac{X * Y}{100}$$

where
- X=% damage by herbicide A at an application rate of x kg/ha;
- Y=% damage by herbicide B at an application rate of y kg/ha;
- E=expected damage by herbicides A and B at an application rate of x+y kg/ha in %

If the observed damage exceeds the calculated expected damage, there is a synergistic effect.

The active compound combinations according to the invention have a herbicidal efficacy which is higher than would have been expected from the observed activities of the individual components when used on their own (calculation according to Colby). Thus, the active compound combinations according to the invention act synergistically. In addition, the synergistic effect is so high that even the added effects of the individual components (without correction according to Colby) are surpassed considerably.

What is claimed is:

1. A method for the selective control of harmful grasses selected from the group consisting of Phalaris spp. in crops of useful plants, which comprises applying a synergistically effective amount of a herbicidal combination comprising:
   A) metribuzin; and
   B) one or more compounds selected from the group consisting of (het)aryloxyphenoxypropionic acids and (het)aryloxyphenoxypropionates.

2. The method according to claim 1, wherein the (het)aryloxyphenoxypropionic acid or (het)aryloxyphenoxypropionate is fenoxaprop, fenoxaprop-P or their ($C_1$–$C_4$)-alkyl, ($C_2$–$C_4$)-alkenyl and ($C_2$–$C_4$)-alkinyl esters.

3. The method according to claim 1 wherein the (het)aryloxyphenoxypropionic acid or (het)aryloxyphenoxypropionate is selected from the group consisting of fenoxaprop, fenoxaprop-P or alkyl esters thereof, diclofop-methyl, fluazifop-P-butyl, haloxyfop-methyl, and quizalofop-ethyl.

4. A method for the selective control of harmful grasses selected from the group consisting of Phalaris spp. in crops of useful plants, which comprises applying a synergistically effective amount of a herbicidal combination comprising:
   A) metribuzin; and
   C) one or more compounds selected from the group consisting of fenoxaprop, fenoxaprop-P, diclofop and ($C_1$–$C_4$)-alkyl, ($C_2$–$C_4$)-alkenyl and ($C_2$–$C_4$)-alkinyl esters thereof.

5. A method for the selective control of harmful grasses selected from the group consisting of Phalaris spp. in crops of useful plants, which comprises applying a synergistically effective amount of a herbicidal combination comprising:
   A) metribuzin; and
   B) one or more herbicides selected from the group consisting of fenoxaprop, fenoxaprop-P-ethyl and diclofop.

6. The method according to claim 5, wherein the combination comprises metribuzin and diclofop.

7. The method according to claim 5, wherein the combination comprises metribuzin and fenoxaprop-P-ethyl.

* * * * *